(12) United States Patent
Eskridge

(10) Patent No.: US 8,876,863 B2
(45) Date of Patent: Nov. 4, 2014

(54) ENDOVASCULAR CLOSURE DEVICE

(71) Applicant: Joe Michael Eskridge, Clyde Hill, WA (US)

(72) Inventor: Joe Michael Eskridge, Clyde Hill, WA (US)

(*) Notice: Subject to any disclaimer, the term of this patent is extended or adjusted under 35 U.S.C. 154(b) by 0 days.

(21) Appl. No.: 14/013,964

(22) Filed: Aug. 29, 2013

(65) Prior Publication Data
US 2013/0345738 A1    Dec. 26, 2013

Related U.S. Application Data

(63) Continuation of application No. PCT/US2012/027259, filed on Mar. 1, 2012.

(60) Provisional application No. 61/448,459, filed on Mar. 2, 2011.

(51) Int. Cl.
A61B 17/08 (2006.01)
A61D 1/00 (2006.01)
A61B 18/08 (2006.01)
A61L 31/02 (2006.01)
A61L 31/04 (2006.01)
A61L 31/10 (2006.01)
A61B 17/12 (2006.01)
A61B 17/00 (2006.01)
A61B 19/00 (2006.01)

(52) U.S. Cl.
CPC .............. A61B 18/08 (2013.01); A61L 31/022 (2013.01); A61L 31/048 (2013.01); A61L 31/10 (2013.01); A61B 17/12022 (2013.01); A61B 17/12113 (2013.01); A61B 17/12172 (2013.01); A61L 2400/16 (2013.01); A61B 2017/00327 (2013.01); A61B 2017/00336 (2013.01); A61B 2017/00477 (2013.01); A61B 2017/00526 (2013.01); A61B 2017/00849 (2013.01); A61B 2017/00853 (2013.01); A61B 2017/00867 (2013.01); A61B 2017/00942 (2013.01); A61B 2017/12063 (2013.01); A61B 2019/5466 (2013.01)
USPC ........................................................ 606/213

(58) Field of Classification Search
USPC ........ 606/108, 198, 200, 213; 623/1.11, 1.23, 623/2.11, 23.72
See application file for complete search history.

(56) References Cited

U.S. PATENT DOCUMENTS

| 7,195,636 | B2 | 3/2007 | Avellanet et al. |
| 7,662,168 | B2 | 2/2010 | McGuckin, Jr. et al. |
| 8,512,399 | B2 * | 8/2013 | Lafontaine .................. 623/2.11 |
| 2007/0191884 | A1 | 8/2007 | Eskridge et al. |
| 2010/0094335 | A1 | 4/2010 | Gerberding et al. |
| 2010/0234878 | A1 | 9/2010 | Hruska et al. |
| 2012/0053596 | A1 * | 3/2012 | Gordon ........................ 606/127 |

FOREIGN PATENT DOCUMENTS

EP    1955661 A2    8/2008

* cited by examiner

Primary Examiner — Melanie Tyson
(74) Attorney, Agent, or Firm — Timothy E. Siegel Patent Law, PLLC; Timothy E. Siegel

(57) ABSTRACT

An aneurysm closure device that includes a retention assembly, adapted to retain the closure device in place on an aneurysm neck. Also, a seal has a wire frame, defining a set of eyeholes and thread, threaded through the set of eyeholes, to form a lattice. Finally, an expanse of silicone, is cured onto the thread, to form a barrier.

7 Claims, 13 Drawing Sheets

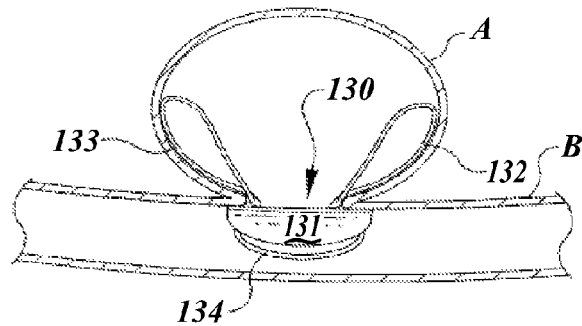
FIG.1D *(Prior Art)*
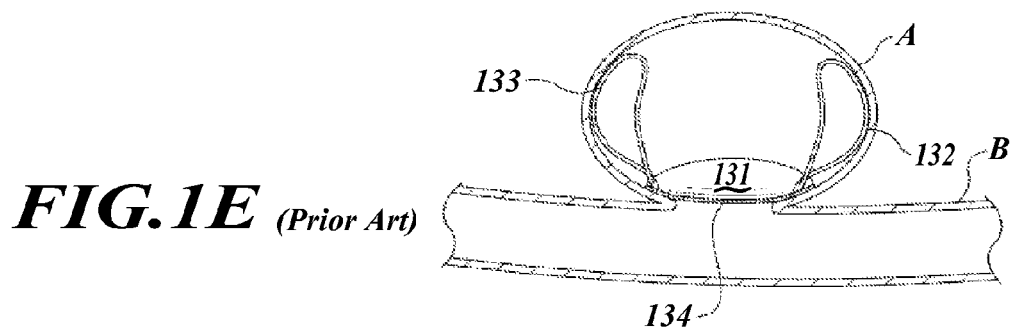
FIG.1E *(Prior Art)*
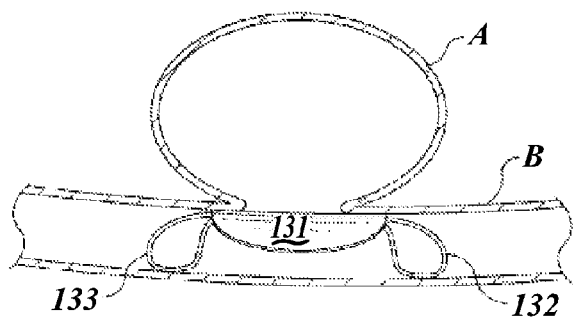
FIG.1F *(Prior Art)*

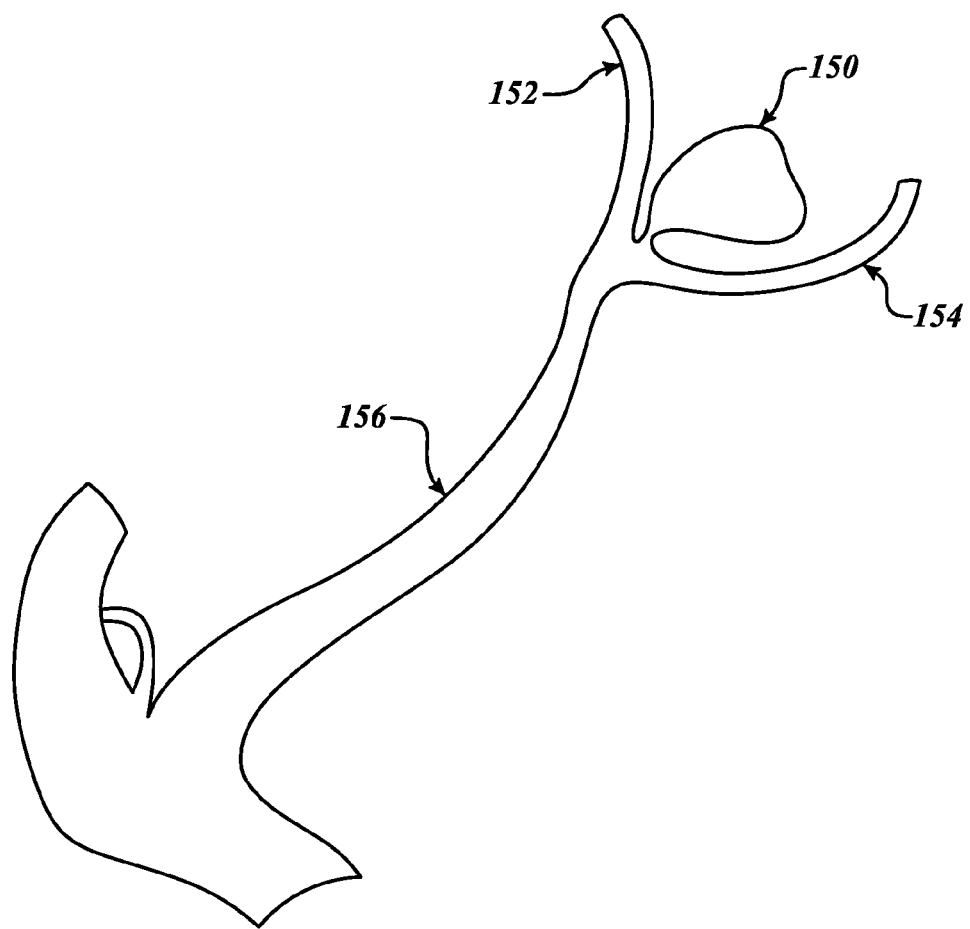
FIG.1G *(Prior Art)*

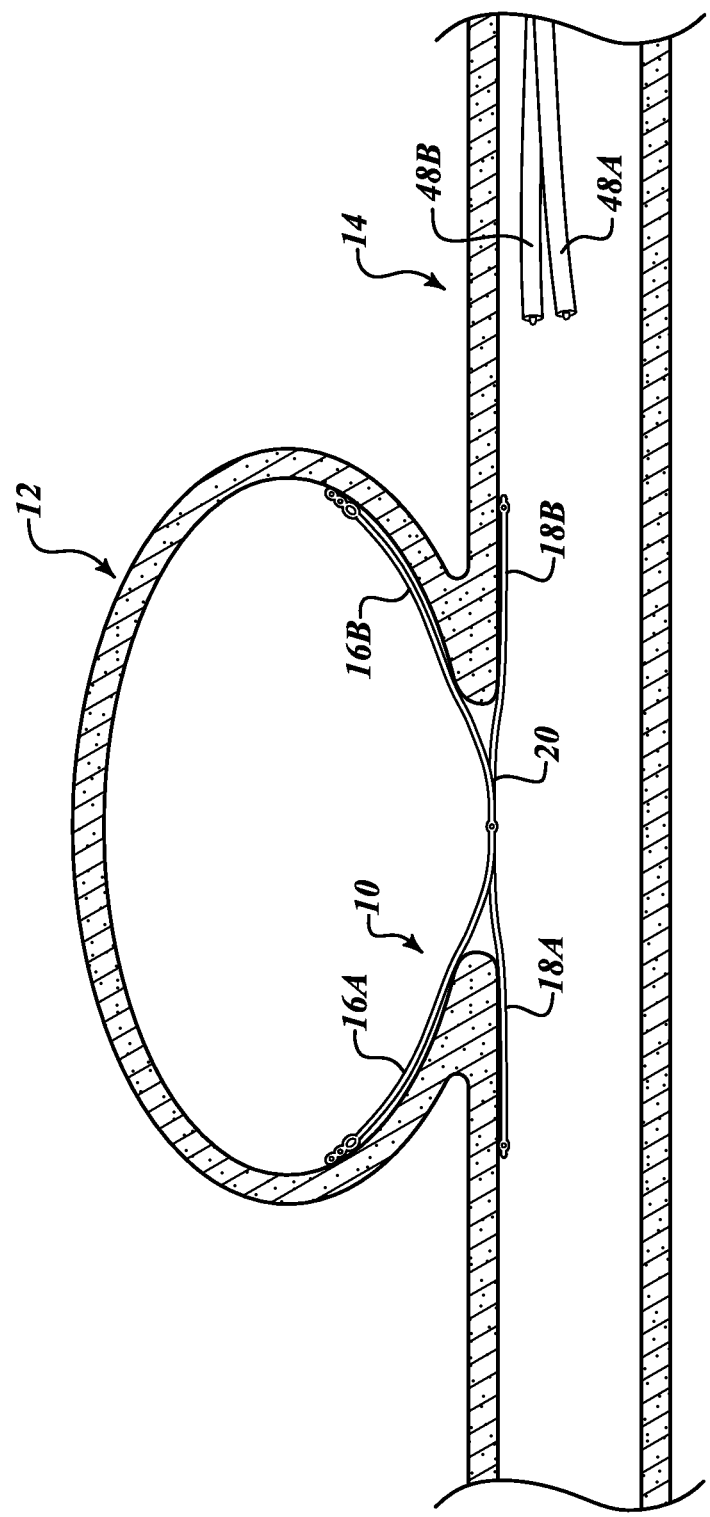

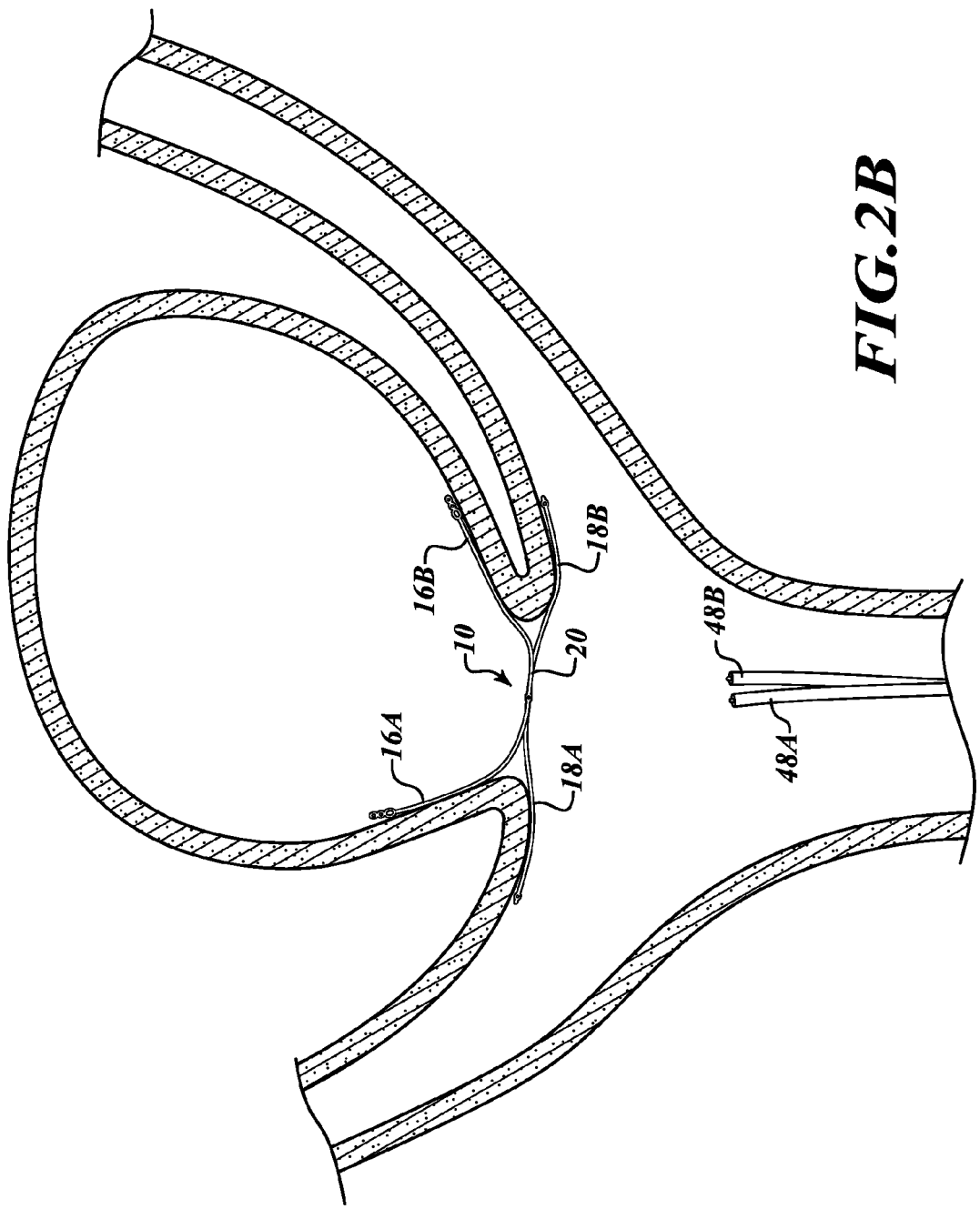

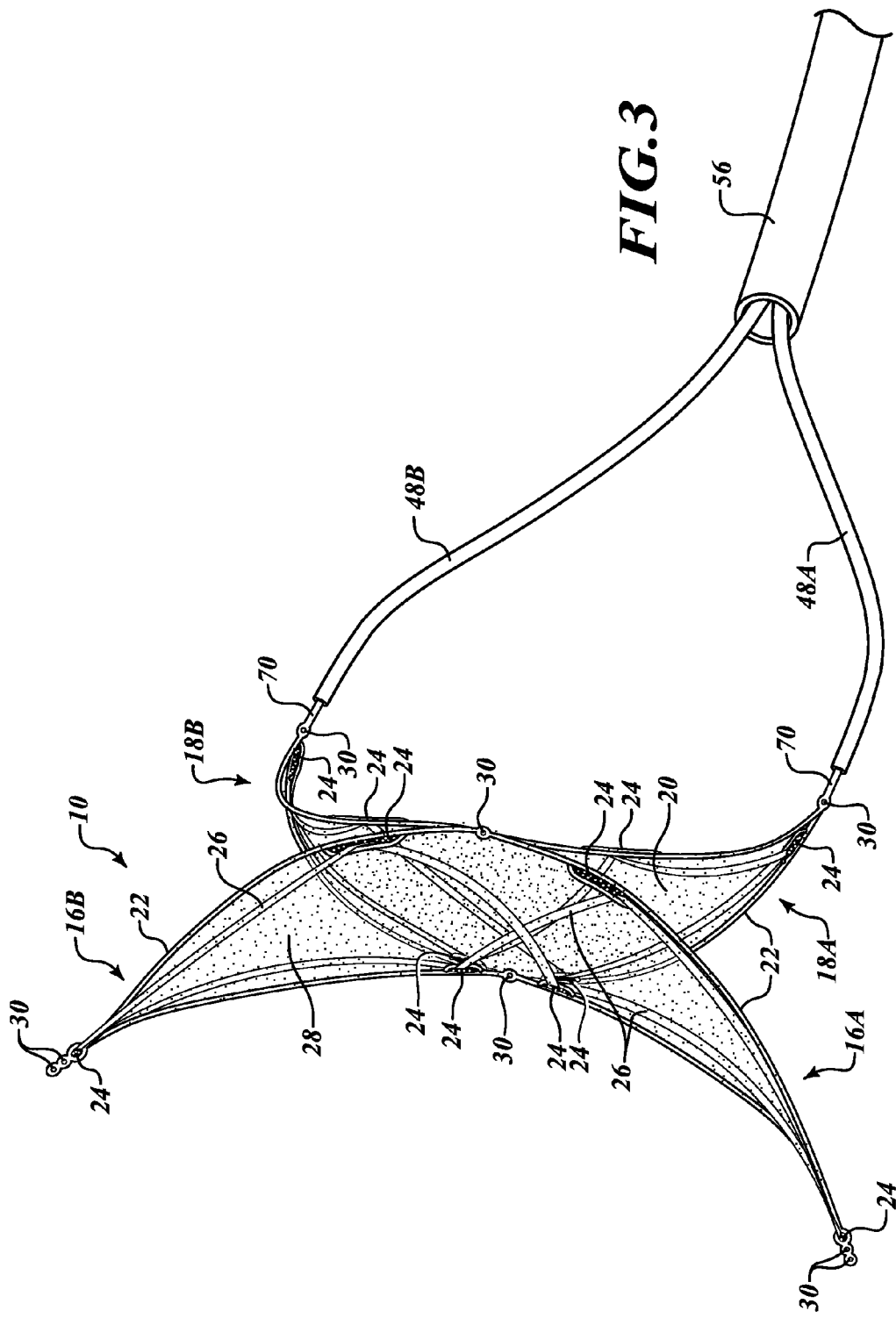

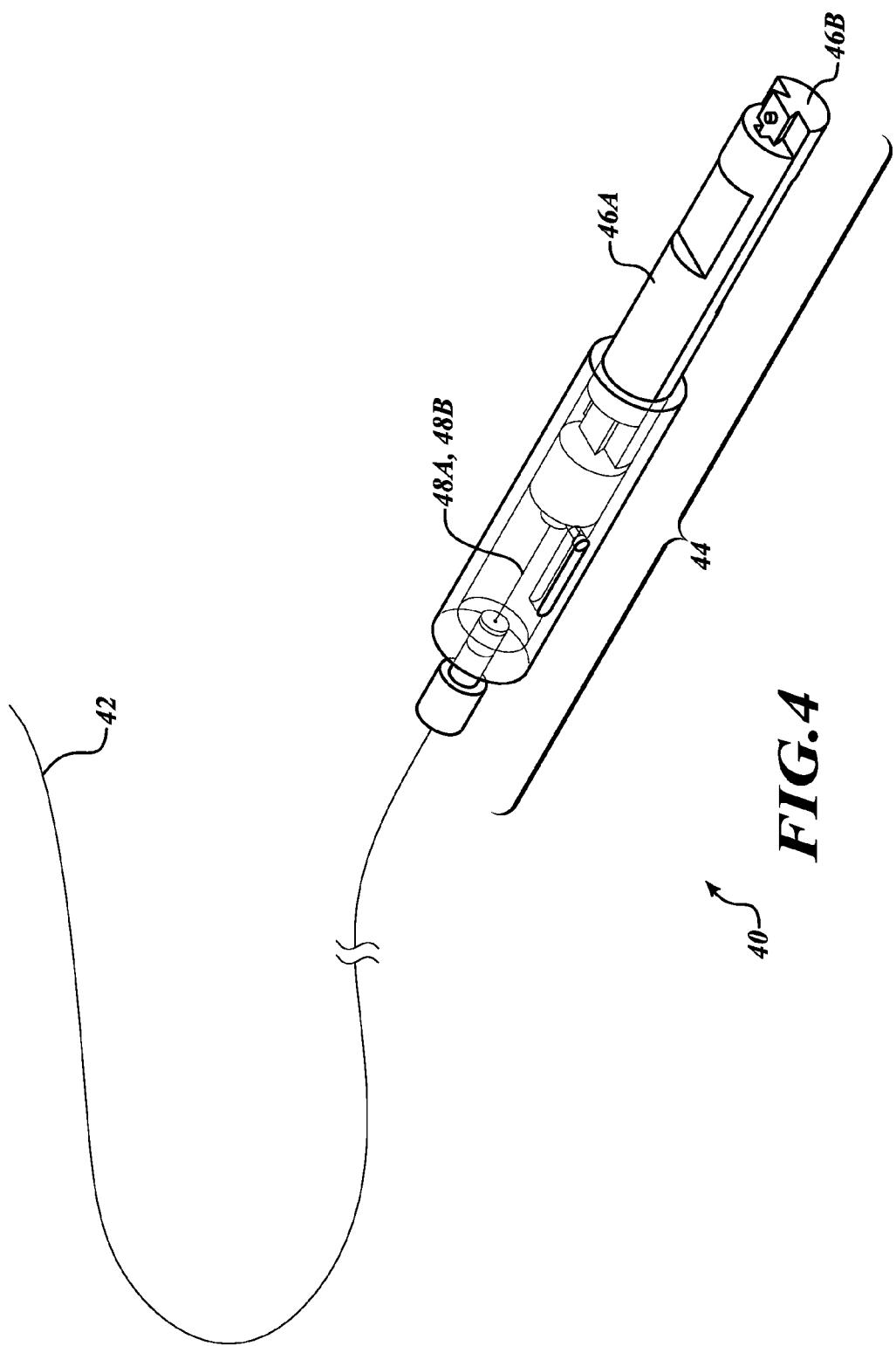

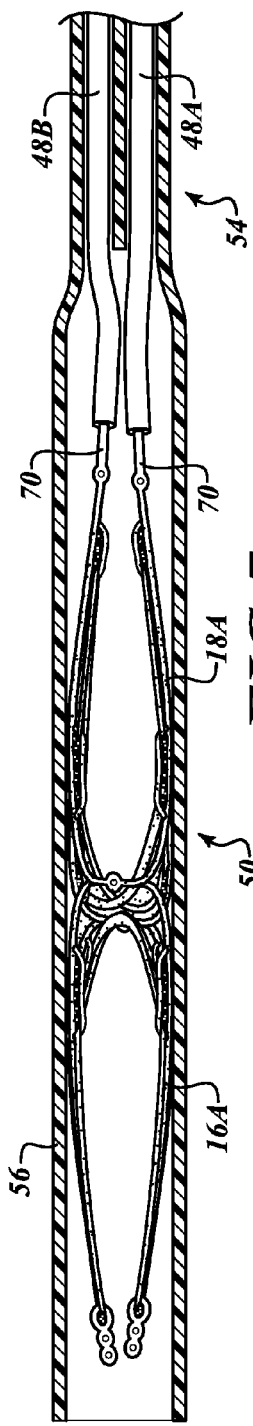
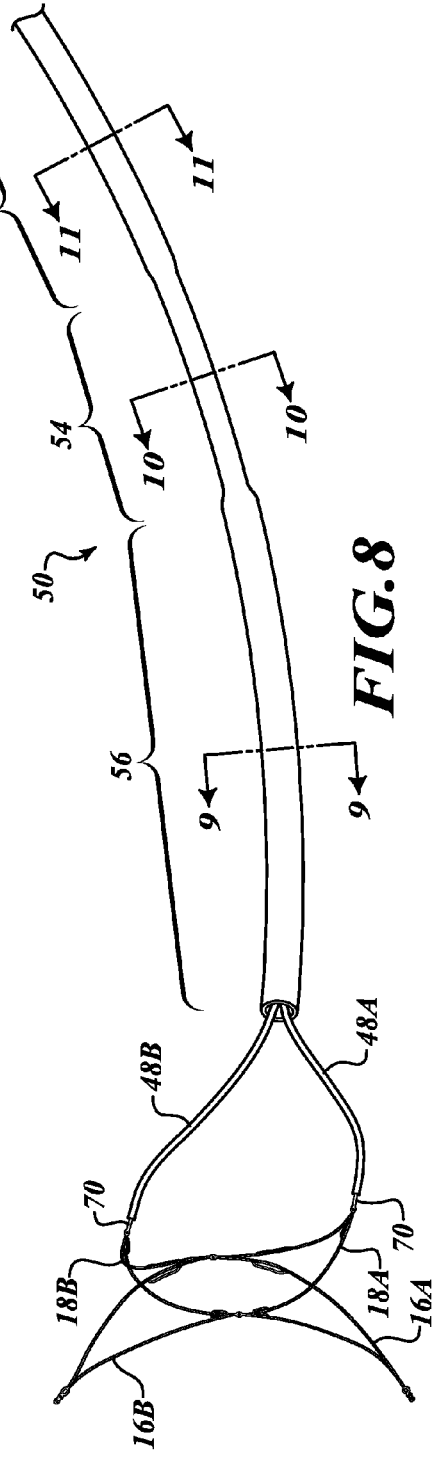
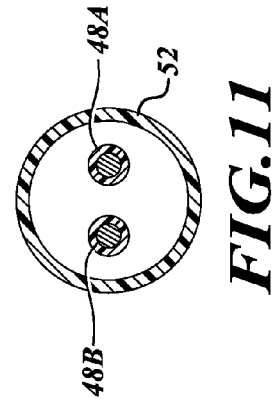
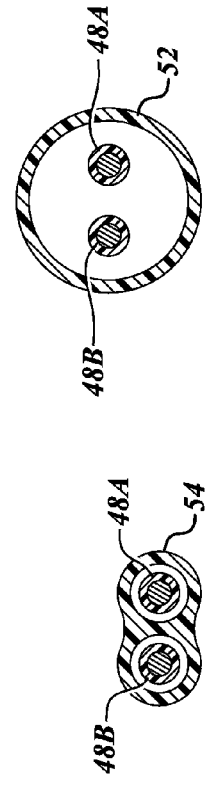
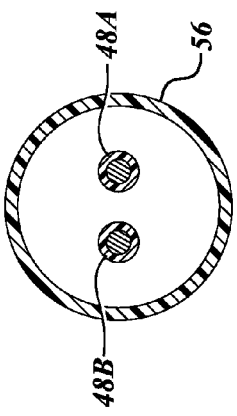
FIG.7
FIG.8
FIG.11
FIG.10
FIG.9

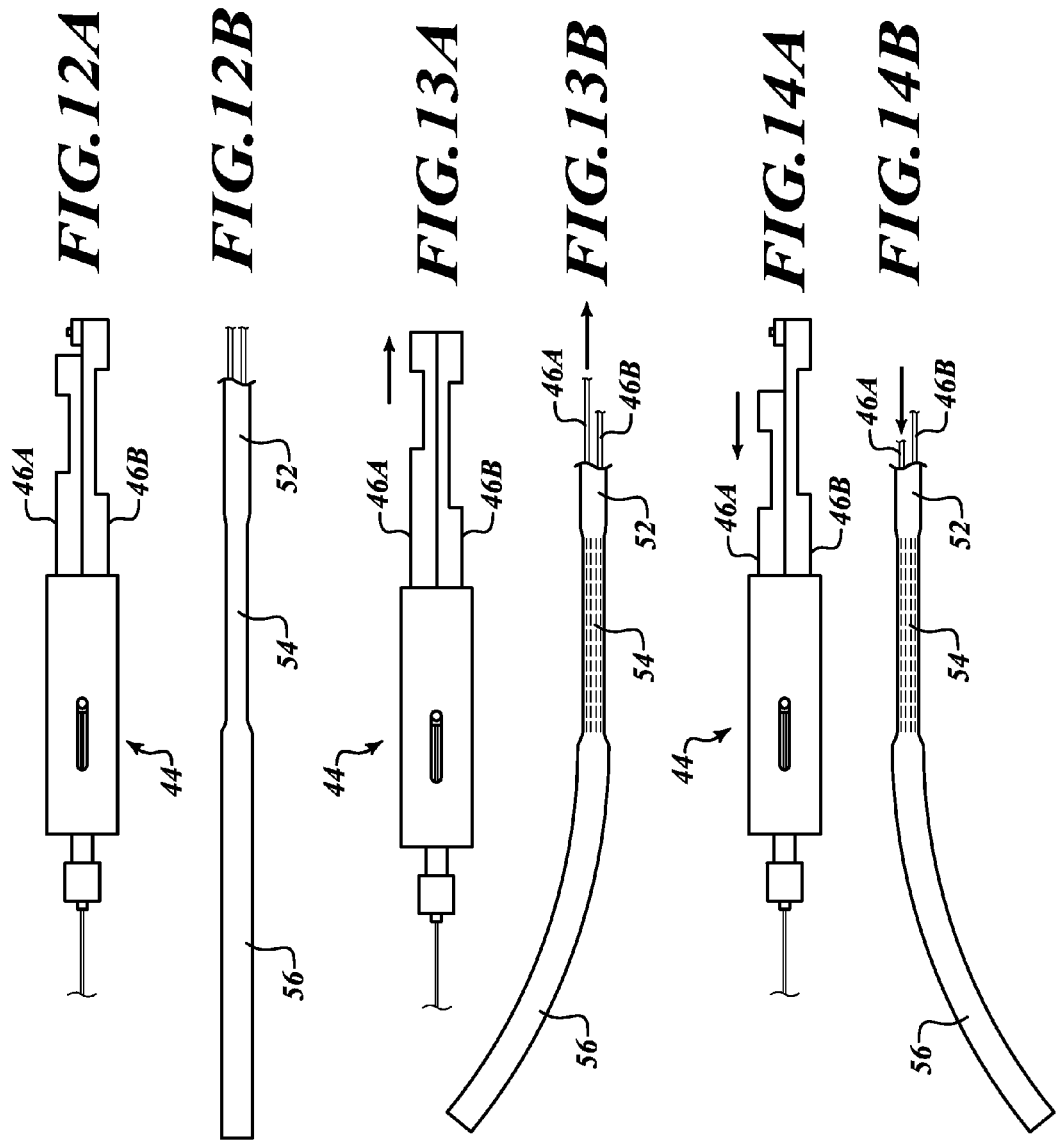

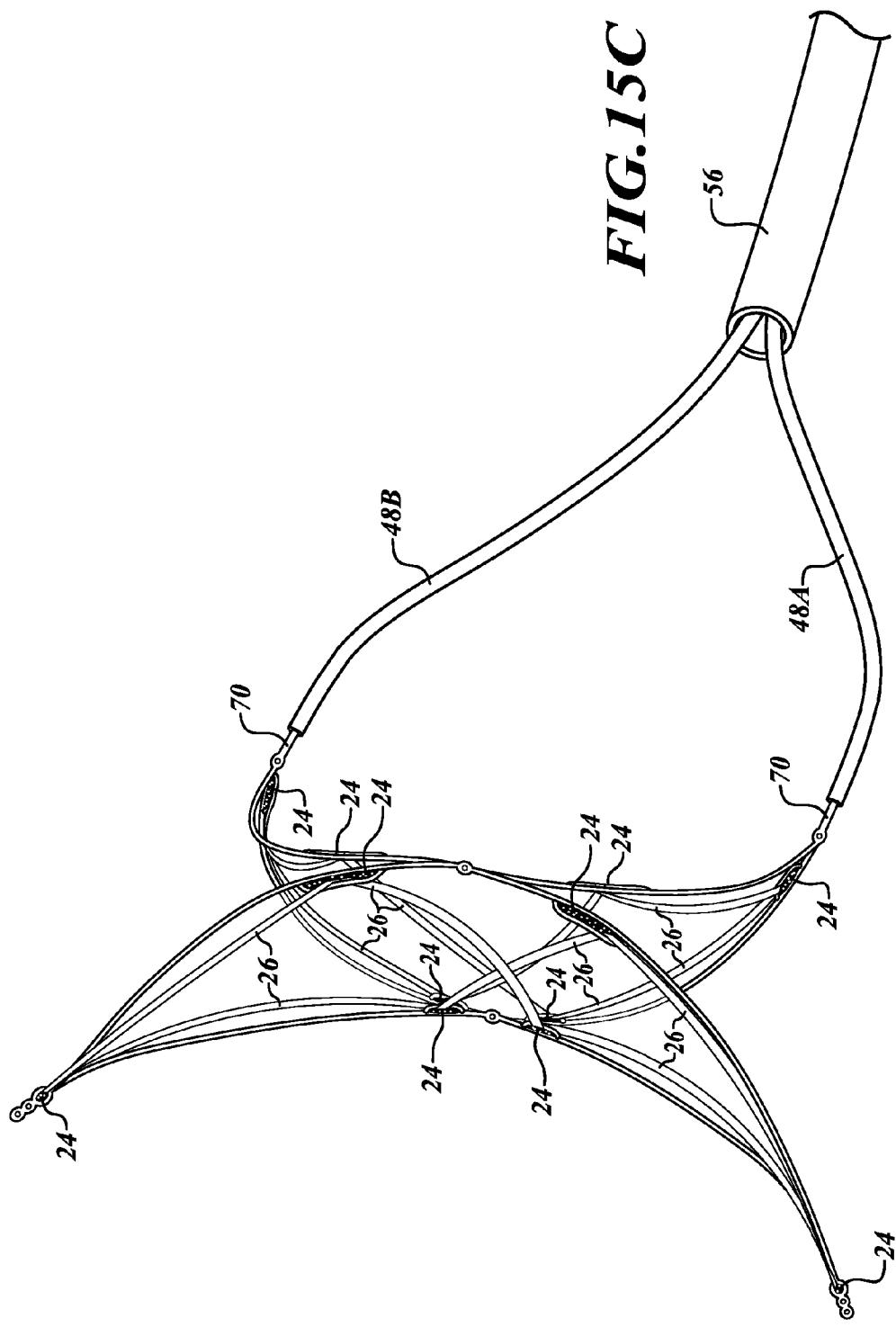

ENDOVASCULAR CLOSURE DEVICE

RELATED APPLICATIONS

This application is a continuation of application serial number PCT/US12/27259, filed on Mar. 1, 2012 which claims priority from provisional application Ser. No. 61/448, 459, filed on Mar. 2, 2011 which are incorporated by reference as if fully set forth herein.

BACKGROUND

The present disclosure is directed to repairing blood vessel defects, such as aneurysms, and other physiological defects or cavities formed in lumens, tissue, and the like, and, more particularly, to an endovascular implantable device and related endoluminal delivery procedure and deployment techniques.

Cranial aneurysms occur when a weakened cerebral blood vessel (root vessel) locally expands to form a bulge or balloon-like enlargement in the vessel wall. These aneurysms can occur along a vessel wall or at locations of vessel branches, such as a T-intersection or V-intersection.

Currently, options for the treatment of brain aneurysms are limited. In one technique, the cranium is opened and a clip is placed at the aneurysm neck to cut off blood flow from the root vessel, thereby reducing swelling and stopping expansion. In another technique, the interior of the aneurysm is accessed by way of a cranial artery, which in turn is reached with a device inserted into the femoral artery. In this technique, coiling material is inserted into the aneurysm, thereby causing clotting which closes off the aneurysm. Both techniques have drawbacks. Opening the cranium always entails some risk. Some locations in the cranium are difficult or impossible to access from the outside. On the other hand, causing clotting in the aneurysm can increase the mass and size of the aneurysm, causing it to press against delicate and critical tissue, and causing further damage.

Devices and techniques have been developed to facilitate treatment of aneurysms. The application herein is a joint inventor on the following U.S. Patent Publication Nos. 2006/0264905 ("Improved Catheters"), 2006/0264907 ("Catheters Having Stiffening Mechanisms"), 2007/0088387 ("Implantable Aneurysm Closure Systems and Methods"), and 2007/0191884 ("Methods and Systems for Endovascularly Clipping and Repairing Lumen and Tissue Defects"). All of these published applications are incorporated by reference herein in their entirety, to the extent legally possible.

For example, referring to FIGS. 1A and 1B, which are reproduced from U.S. Patent Publication No. 2007/0191884, shown therein is a device 130 having a patch or closure structure 131 mounted to or associated with two anchoring structures 132, 133. The closure structure 131 is supported by a framework structure 134 that is provided at least in a perimeter portion and is attached to the closure structure 131 by means of bonding, suturing, or the like. The framework structure 134 is mounted to or associated with the wing-like anchoring structures 132, 133. These anchoring structures 132, 133 in a deployed condition are designed so that at least a portion thereof contacts an inner wall of an aneurysm or an internal wall of an associated blood vessel following deployment.

As can be seen in FIG. 1A, the anchoring structures 132, 133 are generally formed to curve outwardly from an attachment joint 135 to the framework structure 134 and then back inwardly toward one another at the end remote from the attachment point 135. The anchoring loops 132, 133 are generally of the same configuration and same dimension and are located opposite one another as shown in FIG. 1A.

FIG. 1B illustrates a similar device having a closure structure 136 with anchoring structures 137, 138 that attach to or project from a framework structure 139 along opposed, lateral edges of the framework structure. The anchoring structures 137, 138 as illustrated in FIG. 1B are gently curved and, at their terminal sections, extend beyond corresponding terminal sections of the framework structure and the closure structure. The closure and framework structures in this embodiment are generally provided having a surface area that exceeds the surface area of the aneurysm neck, and the anchoring structures generally reside inside the aneurysm following placement of the device. In this configuration, the anchoring structures exert lateral and downward force on the closure structure so that it generally conforms to the profile of the vessel wall at the site of the aneurysm, thereby sealing the neck of the aneurysm from flow in the vessel and providing reconstruction of the vessel wall at the site of the aneurysm. Unfortunately, framework structure 139 and structures 137 and 138 are mismatched in length and are too stiff to apply the mutually opposing forces on interposed tissue, necessary to form an effective clip. In addition this structure is too stiff and expanded to be able to collapse into a configuration that can be fit into the space available in a placement device, small enough to be introduced into the smaller cranial blood vessels. Moreover, its boxy shape makes it difficult to maneuver as is necessary to effect placement into an aneurysm.

FIGS. 1C-1F schematically illustrate the devices of FIGS. 1A and 1B deployed at the site of an aneurysm. A bulge in the blood vessel B forms an aneurysm A. As shown in FIGS. 1C and 1D, when the device 130 is deployed across the neck of and within the aneurysm A, the closure structure 131 is positioned to cover the opening of the aneurysm and the anchoring structures 132 and 133 are retained inside and contact an inner aneurysm wall along at least a portion of their surface area. In this fashion, the closure structure 131 and the framework portion 134 are supported across the aneurysm opening and are biased against the neck of the aneurysm from outside the aneurysm.

In the embodiment illustrated in FIGS. 1C and 1D, the closure structure 131 and the framework portion 134 are deployed outside the internal space of the aneurysm. In an alternative embodiment illustrated in FIG. 1E, the closure structure 131 and the framework portion 134 are supported across the aneurysm opening and biased against the neck of the aneurysm from inside the aneurysm.

FIG. 1F illustrates an alternative deployment system and methodology, wherein a device having at least two anchoring structures is deployed such that the closure structure 131 is positioned to cover the opening of the aneurysm, and the anchoring structures 132, 133 are positioned outside the aneurysm and contact an inner blood vessel wall B in proximity to the aneurysm. In this embodiment, the anchoring structures 132, 133 may be generally sized and configured to match the inner diameter of the vessel in proximity to the neck of the aneurysm so that following deployment the anchoring structures contact the vessel wall in a substantially continuous manner without straining or enlarging the vessel wall in the area of the aneurysm. In all of these embodiments, following placement of the device, the closure structure substantially covers the aneurysm neck to effectively repair the vessel defect. The anchoring structures do not substantially interfere with flow of blood in the vessel.

As can be seen in the foregoing, the structures may be difficult to place, particularly in the circuitous blood vessel network of the brain. For the typical aneurysm, extending in a perpendicular manner from its root blood vessel, it may be a challenge to insert the structure into the aneurysm. Moreover, for the device to seal or close the aneurysm, the anchoring structures must mutually press against the aneurysm sides. If one side wall of an aneurysm is not well suited for supporting an anchoring structure, the anchor for the opposite side will not be well supported to provide sufficient pressure on this opposite side wall. This problem drives the design of anchor structures 132 and 133 to be larger, to facilitate receiving sufficient support from the aneurysm interior surface. This, in turn, has the potential to create a mass effect problem, in which the mass of the structures 132 and 133, plus any clotting that occurs around them, causes the aneurysm to become more massive, potentially pressing against delicate nervous system tissue as a result.

Moreover, the situation is even more difficult for aneurysms formed at the intersection of vessels, such as a T-intersection or V-intersection. FIG. 1G illustrates a saccular bifurcation aneurysm 150 appearing at the intersection of two vessels 152, 154, branching from a stem vessel 156. Cerebral bifurcation aneurysms are commonly found at the middle cerebral artery, internal carotid artery, anterior communicating artery, basilar artery, posterior communicating artery, and other locations.

Typically, to place device 130 into a blood vessel of the brain requires a number of steps. First, an incision is made into the femoral artery and a sheath is introduced, extending approximately to the aorta. A first guide catheter is inserted through the sheath and extended up into the carotid artery. A second guide catheter is coaxially introduced through the first guide catheter and extended up into the target aneurysm. Both guide catheters are introduced using a guide wire having a steerable tip of either stainless steel or nitinol. Then, microcatheter introducer is inserted through the guide catheter, to the aneurysm, and device 130 is placed at the aneurysm site. Heretofore, however, once reaching the aneurysm there has been no effective method for positioning a device that requires precise positioning. A device that would require a definite orientation, at least partially inside the aneurysm, presents particular challenges in positioning during implantation.

Another difficulty in delivering a complex implant into an aneurysm is the lack of space to pack such an implant in a lumen at the end of a microcatheter. Any such device must fold into a cylinder having an internal diameter on the order of 1 mm and a length of about 10 mm. Upon delivery it must expand to anchor itself in place and to seal an area that could be as large as 10 mm². The seal over the neck of the aneurysm although thinner than 1 mm, must be strong enough to affirmatively occlude the aneurysm, with a very high degree of certainty.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of an aneurysm closure device that includes a retention assembly, adapted to retain the closure device in place on an aneurysm neck. Also, a seal has a wire frame, defining a set of eyeholes and thread, threaded through the set of eyeholes, to form a lattice. Finally, an expanse of silicone, is cured onto the thread, to form a barrier.

In a second separate aspect, the present invention may take the form of a method of making an aneurysm closure device, includes forming a wire frame that defines eyeholes and threading an ePTFE fiber through the eyeholes to form a lattice, which is coated with raw silicone. Finally, the silicone is cured to form a seal. In another preferred embodiment two sheets of silicone, cut to the correct dimensions, are adhered together about the ePTFE fiber.

In a third separate aspect, the present invention takes the form of a microcatheter assembly for implanting a medical device at a location in the blood vessel network of a patient. The assembly includes a flexible microcatheter that has a proximal single lumen portion, extending for at least 80% of the extent of the tube and a medial double lumen portion, immediately distal to the proximal single lumen portion, and being between 1 mm and 200 mm in length. A distal single lumen portion, holds the medical device in a contracted state. Also, first and second wires, extend through the tube and are separated into separate lumens in the medial double lumen portion and being connected to the medical device at two separate points. In addition, a control unit, having a first wire control handle affixed to the first wire and a second wire control handle affixed to the second wire. Each control handle is capable of pushing its affixed wire distally through the tube or retracting its wire proximally through the tube. Also, the first and second wire control handles can be rotated together to any rotational position. Accordingly, the wires may be advanced in a distal manner to push the medical device out of the distal lumen and the medical device may then be manipulated by changing relative position of the control handles both in translation and rotation to manipulate and implant the medical device.

In a fourth separate aspect, the present invention may take the form of a method of implanting a medical device at a blood vessel location in a patient that utilizes a microcatheter assembly that has a flexible microcatheter tube, including: a proximal single lumen portion, extending for at least 80% of the extent of the tube; a medial double lumen portion, immediately distal to the proximal single lumen portion, and being between 1 mm and 200 mm in length; a distal single lumen portion, holding the medical device in a contracted state; first and second wires, extending through the tube and separated into separate lumens in the medial double lumen portion and being connected to the medical device at two separate points, and wherein the two wires at the two separate points are detachable from said medical device. Also, a control unit has a first wire control handle affixed to the first wire and a second wire control handle affixed to the second wire, each control handle being capable of pushing its affixed wire distally through the tube or retracting its wire proximally through the tube, and where the first and second wire control handles can be rotated together to any rotational position. A guide catheter is introduced, extending from an incision into a blood vessel, to a target location for the medical device. Then the microcatheter tube is pushed through the guide catheter so that the distal portion is at the target location. Finally the medical device is pushed out of the microcatheter tube and control unit is used to manipulate the medical device until it is positioned correctly at the target location. Finally, detaching said two wires from said medical device and withdrawing the microcatheter tube and the guide catheter from the patient.

In addition to the exemplary aspects and embodiments described above, further aspects and embodiments will become apparent by reference to the drawings and by study of the following detailed descriptions.

BRIEF DESCRIPTION OF THE SEVERAL VIEWS OF THE DRAWINGS

Exemplary embodiments are illustrated in referenced drawings. It is intended that the embodiments and figures disclosed herein are to be considered illustrative rather than restrictive.

FIGS. 1C, 1D, 1E, and 1F schematically illustrate the devices of FIGS. 1A and 1B deployed at the site of an aneurysm;

FIG. 1G illustrates a saccular bifurcation aneurysm;

FIG. 2A is a sectional side view of an aneurysm closure device, according to the present invention, installed in the neck of an aneurysm that has developed at the side of a blood vessel.

FIG. 2B is a sectional side view of the aneurysm closure device of FIG. 2A, according to the present invention, installed in the neck of an aneurysm that has developed at a Y-intersection of blood vessels.

FIG. 3 is an isometric view of the aneurysm closure device of FIG. 2A.

FIG. 4 is an isometric view of an implantation catheter, according to the present invention, with the closure device of FIG. 2A retracted.

FIG. 7 is a sectional side view of the distal end of the catheter of FIG. 4, with the closure device of FIG. 2A retracted.

FIG. 8 is an isometric view of the distal portion of the positioning assembly of FIG. 4, with the closure device of FIG. 2A extended.

FIG. 9 is a cross-sectional view of the distal portion of FIG. 8, taken at view line 9-9.

FIG. 10 is a cross-sectional view of the distal portion of FIG. 8, taken at view line 10-10.

FIG. 11 is a cross-sectional view of the distal portion of FIG. 8, taken at view line 11-11.

FIG. 12A is a side view of the user control of FIG. 6, set in a neutral position.

FIG. 12B is a side view of the user control of the distal end of FIG. 7, corresponding to the user control setting of FIG. 12A.

FIG. 13A is a side view of the user control of FIG. 6, set in a skewed position.

FIG. 13B is a side view of the user control of the distal end of FIG. 7, corresponding to the user control setting of FIG. 13A.

FIG. 14A is a side view of the user control of FIG. 6, set in a position skewed opposite to that of FIG. 13A.

FIG. 14B is a side view of the user control of the distal end of FIG. 7, corresponding to the user control setting of FIG. 12A.

FIG. 15C is an isometric view of a work piece shown connected to the distal end of FIG. 7 for ease of presentation and representing a further stage in the manufacturing of the closure device of FIG. 3.

DETAILED DESCRIPTION OF THE PREFERRED EMBODIMENTS

Figure 1A:
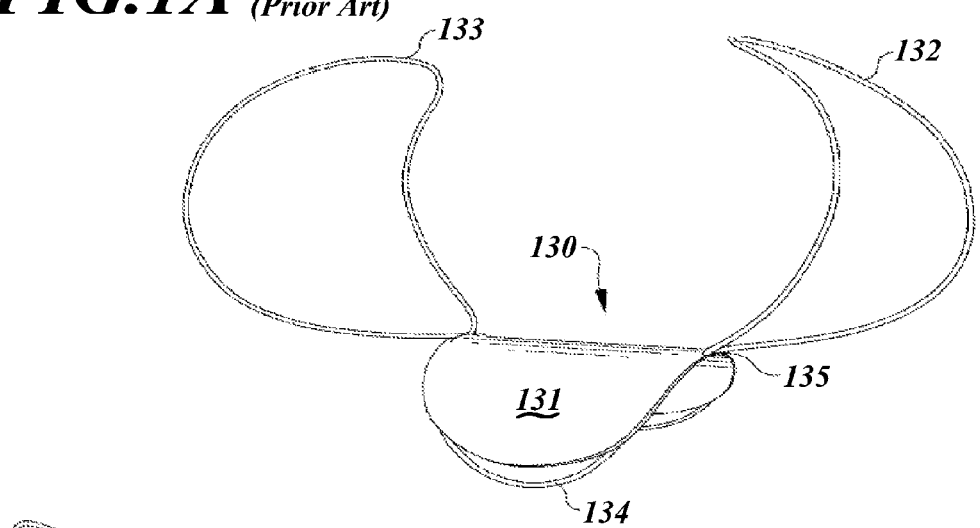
FIG. 1A illustrates an enlarged schematic front isometric view of a known implantable device in a deployed condition.
Figure 1B:
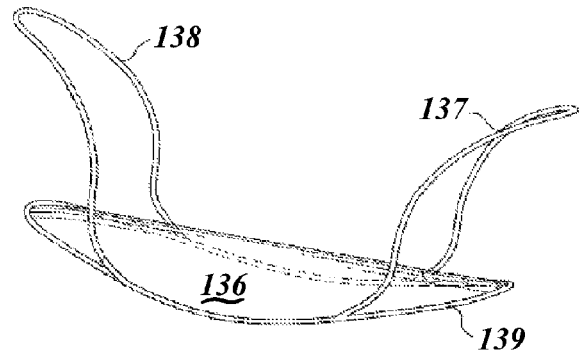
FIG. 1B illustrates an enlarged schematic front isometric view of another known implantable device in a deployed condition.
Figure 1C:
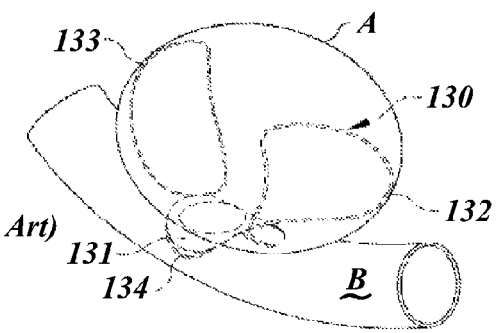
Figure 5:
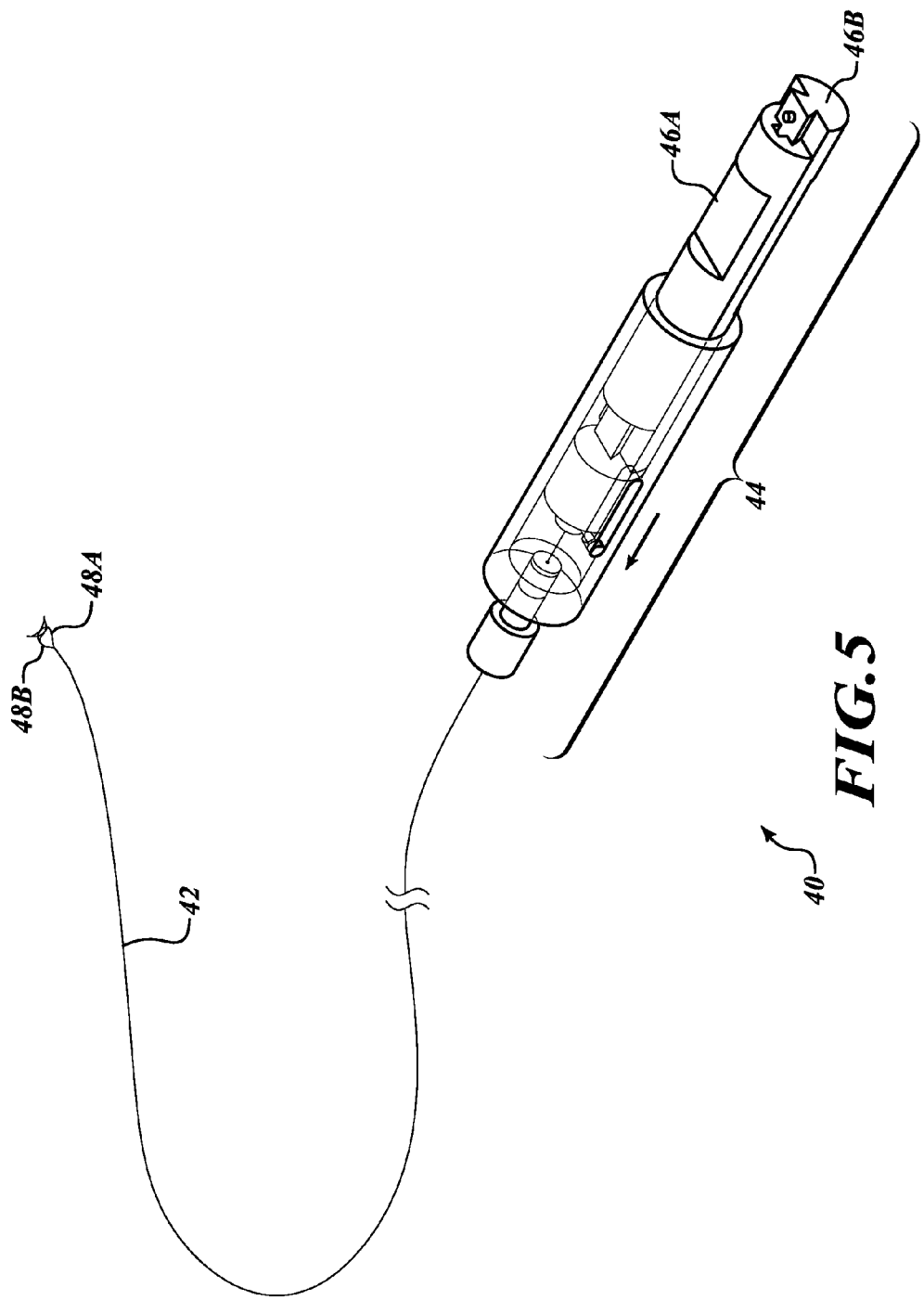
FIG. 5 is an isometric view of the catheter of FIG. 4, with the closure device of FIG. 2A exposed.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures or components or both associated with endovascular coils, including but not limited to deployment mechanisms, have not been shown or described in order to avoid unnecessarily obscuring descriptions of the embodiments.

Unless the context requires otherwise, throughout the specification and claims that follow, the word "comprise" and variations thereof, such as "comprises" and "comprising" are to be construed in an open inclusive sense, that is, as "including, but not limited to." The foregoing applies equally to the words "including" and "having."

Reference throughout this description to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same embodiment.

Furthermore, the particular features, structures, or characteristics may be combined in any suitable manner in one or more embodiments.

The present disclosure is directed to closing a bulge or aneurysm formed in blood vessel, such as an artery or vein (referred to more generally herein as "vessel"), in a manner that does not suffer from some of the drawbacks of prior art methods. For example, in the prior art method involving the insertion of a wire coil into the aneurysm, the resultant blood clot can create problems through its mass and the possibility of pressing against nearby nerves. In addition, the wire coil can have the effect of keeping the neck open, possibly causing another aneurysm to form.

The embodiments of the present disclosure combine the closure structure and the anchoring structure into a single unit to improve compactness, allow delivery into the tortuous intracranial circulation system via a microcatheter, and to improve the aneurysm neck closure. In addition, the embodiments of the present disclosure provide enhanced rotation control and placement of the device within the aneurysm via two attachment points for a microcatheter. Moreover, markers can be used at the junctions of the device structure to aid in tracking the movement of the closure device during insertion and placement.

Referring to FIG. 2A, a preferred embodiment of an aneurysm closure device 10 is shown in its implanted environment of an aneurysm 12 attached to a root vessel 14. FIG. 2B shows the device 10, implanted environment, on an aneurysm that has developed at a Y-intersection of blood vessels. FIG. 3 shows a more detailed perspective view of closure device 10. In FIG. 2A, aneurysm closure device 10 is held in place by four anchors: A first aneurysm anchor 16A and a first root vessel anchor 18A mutually anchor closure device 10 to a distal side of the aneurysm 12, while a second aneurysm anchor 16B and a second root vessel anchor 18B, mutually anchor closure device 10 on a proximal side of the aneurysm 12. Referring to FIG. 3, it is seen that in the installed state of FIG. 2A, a seal 20 is placed over the neck of aneurysm 12, thereby preventing further blood flow into aneurysm 12 and causing it to atrophy over time.

First anchors 16A and 18A act as a first clip, mutually applying gentle pressure toward each other, thereby clipping about the interposed tissue. In similar manner, second anchors 16B and 18B act as a second clip. Working together, anchors 16A, 18A, 16B and 18B hold the seal 20 in place, thereby blocking the flow of blood into aneurysm 12.

Figures 15A, 15B:
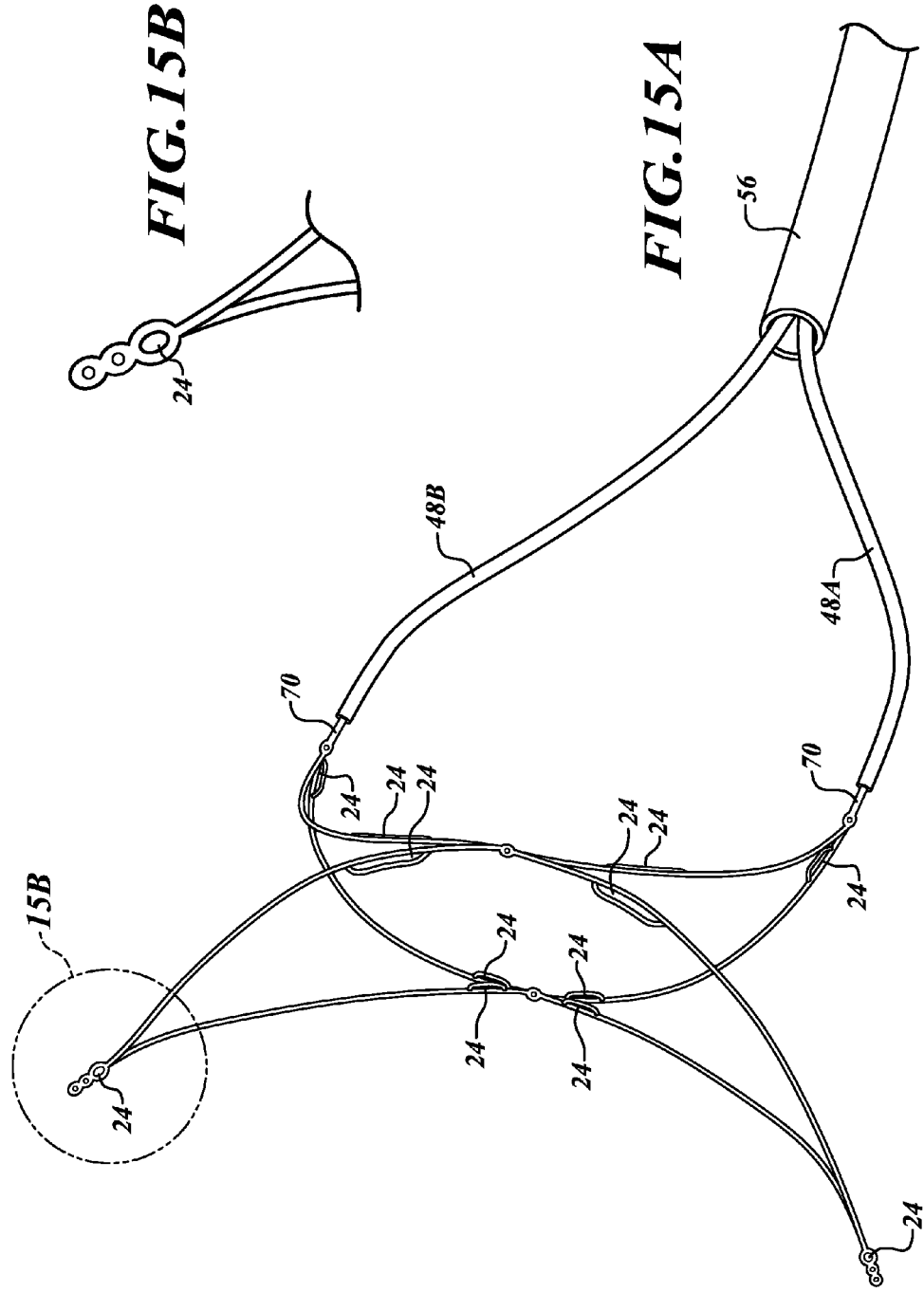
FIG. 15A is an isometric view of a work piece shown connected to the distal end of FIG. 7 for ease of presentation and representing a stage in the manufacturing of the closure device of FIG. 3.
FIG. 15B is a detail view of a portion of FIG. 15A, as indicated by circle 15B, in FIG. 15A.

Closure device 10 includes a wire frame 22, which is made of nitinol, or some other shape-memory material. Prior to use, closure device 10 is maintained at a temperature below human body temperature, thereby causing wire frame to assume the shape shown in FIG. 3, when first pushed out of terminal lumen 56. In one preferred embodiment, after warming to 37 C, however, anchors 16A and 18A, are urged together, as are anchors 16B and 18B, thereby more securely clipping to the interposed tissue. In another preferred embodiment, however, the natural spring force of the nitinol causes device 10 to expand when it is pushed out of fossa 56, and it retains this shape during positioning and use. A set of eyeholes 24 are defined by frame 22 and expanded poly tetrafluoroethylene (ePTFE) thread or fiber 26 is threaded into these eyeholes 24 to form a lattice. The eyeholes 24 are filled with gold solder (FIG. 15B), thereby anchoring thread 26 and closing eyeholes 24. Accordingly, although materials may be useable as thread 26 whatever material is used must be capable of withstanding the temperature of molten gold solder, which is typically 716° C. The ePTFE lattice work 26 is then coated with silicone 28, which in one preferred embodiment is cured in situ to form the seal 20. In another preferred embodiment, sheets of silicone are cut to the correct dimensions and adhered together about the ePTFE lattice 26. In the embodiment shown, silicone 28 is placed on the aneurysm anchors 16A and 16B, but in an alternative embodiment, the ePTFE portion on anchors 16A and 16B are there to complete the threading arrangement, but are not coated with silicone. In another alternative preferred embodiment more, and smaller, eyeholes 24 are defined. In a preferred embodiment, two spots of radiopaque material 30 are placed at the tip of each aneurysm anchor 16A and 16B and one spot of radiopaque material 30 is placed at the tip of each root vessel anchor 18A and 18B. Accordingly, a surgeon placing closure device 10 can determine the position of closure device 10, through a sequence of X-ray images, relative to the contours of the aneurysm 12, which is shown by the use of a radiopaque dye, placed into the bloodstream.

In an alternative preferred embodiment at least some of the anchors, serving the function of anchors 16A-18B, are made of a thin sheet of nitinol, or a thin sheet of nitinol covered with a biocompatible silicone, or polymeric material, for forming a good grip on the tissue it contacts. In yet another embodiment, at least some of the anchors are made entirely of polymeric material. In an additional preferred embodiment, ePTFE thread 26 lattice, is replaced with metal filigree, made of a metal such as gold, having a high melting point. In addition, there is a broad range of engineered materials that can be created for this type of purpose. In yet another preferred embodiment, anchors, serving the function of anchors 16A-18B, are made of wire loops or arcs, some of which support an ePTFE reinforced silicone barrier, thereby providing a closure mechanism for an aneurysm.

Referring to FIGS. 4-14B, prior to installation, closure device 10 forms a part of a micro-catheter closure device installation assembly 40, which although specifically adapted to install closure device 10 at an aneurysm also embodies mechanisms that could be used for other tasks, particularly in accessing tissue through a blood vessel. Assembly 40 comprises a micro-catheter subassembly 42, and a user-control subassembly 44. A first wire-head handle 46A and a second wire-head handle 46B, are attached to a first wire 48A and a second wire 48B, respectively.

Referring to FIGS. 7-14B, in micro-catheter subassembly 42, wires 48A and 48B pass through a flexible tube 50, which has an exterior diameter of about 1.5 mm, and which has a hydrophilic exterior surface, to aid in progressing toward a blood vessel destination. Tube 50 is divided into a proximal single lumen extent 52, near-distal dual lumen extent 54, and a distal fossa or wide-lumen extent 56. This construction permits for the control of the shape and orientation of distal portion of tube 50, and for the positioning of closure device 10, after it has been pushed out of fossa 56. As shown in FIGS. 13A and 13B, if the first wire-head handle 46A is retracted relative to second wire-head handle 46B, then distal fossa 56 bends towards handle 46A. Likewise, as shown in FIGS. 14A and 14B, if the second wire-head handle 46B is retracted relative to first wire-head handle 46A, then distal fossa 56 bends towards handle 46B. The orientation of fossa 56, and the direction it turns to when handle 46A or 46B is retracted, can be changed by rotating the wire-head handles 46A and 46B, together. After closure device 10 is pushed out of fossa 56, it responds in like manner, bending toward wire-head handle 46A, when handle 46A is retracted, and toward handle 46B, when handle 46B is retracted. It can be rotated, and the direction that it bends when wire 46A or 46B is pulled can be determined, by rotating the handles 46A and 46B, together. This freedom in positioning is important during the implantation process, when as shown in FIGS. 2A and 2B anchors 16A and 16B must be maneuvered through the neck of the aneurysm 12, and positioned so that they extend along the same dimension as root vessel 14. The radiopaque markings 30 (FIG. 3) are invaluable during this process.

Figure 6:
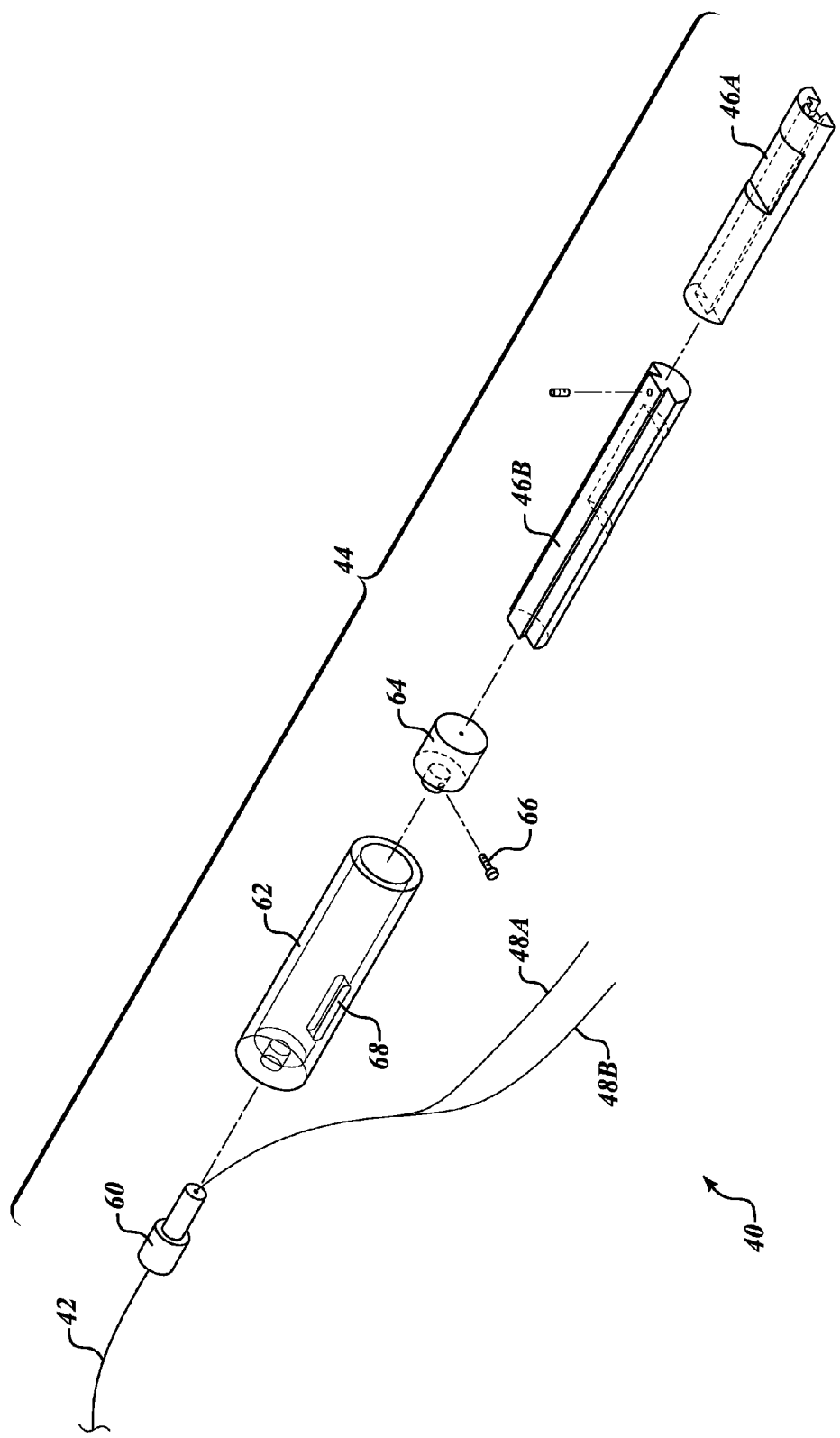
FIG. 6 is an isometric exploded view of the user control portion of the catheter of FIG. 4.

Referring now to FIG. 6, subassembly 42 is threaded through an end cap 60, and passes into a transparent chamber 62, where wires 48A and 48B, emerge from tube 50, pass through a slider 64 and are separately anchored in handles 46A and 46B, respectively. The travel extent of slider 64 is limited by a stop pin 66 and a slot 68.

Wires 48A and 48B each include a region 70 (FIGS. 7 and 8) that is susceptible to electrolytic disintegration. To detach closure device 10, after placement, an electric current is passed through wires 48A and 48B, causing regions 70 to electrolytically disintegrate, freeing closure device 10 from wires 48A and 48B, so that it can be left in place in its target location, sealing aneurysm 12. In a preferred embodiment, handles 46A and 46B each includes an electrical contact connected to wire 48A and 48B, respectively, for attaching to a source of electricity for performing the above-described step.

Skilled persons will readily recognize, from the drawings and the above text, that a point on the region 70 of first wire 48A constitutes a first attachment point to aneurysm seal 20, which is a type of medical device. Likewise, a point on the region 70 of second wire 48B, constitutes a second attachment point to seal 20, which is spaced apart from the first attachment point. Such persons will further recognize that first wire 48A can be used to either push or pull the first attachment point and second wire 48B can be used to either push or pull the second attachment point.

Subassembly 42 is introduced into the femoral artery and guided through the carotid artery into the brain's arterial system, and further guided to the aneurysm 12. At this point closure device 10 is pushed out of fossa 56, anchors 16A and 16B are guided into aneurysm 12, and anchors 18A and 18B are positioned in root artery 14. Then a pulse of electricity severs closure device 10 from wires 48A and 48B and closure device 10 is installed in place.

Wires 48A and 48B are made of stainless steel alloy 304, which may also be referred to as alloy 18-8. This material is coated with poly tetrafluoroethylene, except for at detachment points 70 and the points where they are connected to a source of electricity. The nitinol alloy that frame 22 (FIG. 3) is made of is 54.5% to 57% nickel, with the remainder titanium, which forms a super-elastic alloy. The introducer tube 50 is made of high density polyethylene, coated at the distal tip with a hydrophilic coating. Finally, the silicone 28 of the closure device 10 is silicone MED 4820 or MED-6640, which is a high tear strength liquid silicone elastomer, having a Shore A durometer reading of 20-40. A MED6-161 Silicone Primer is used to attach silicone 28 to Nitinol frame 22.

While a number of exemplary aspects and embodiments have been discussed above, those possessed of skill in the art will recognize certain modifications, permutations, additions and sub-combinations, thereof. It is therefore intended that the following appended claims and claims hereafter introduced are interpreted to include all such modifications, permutations, additions and sub-combinations as are within their true spirit and scope.

The invention claimed is:

1. A microcatheter assembly for implanting a medical device at a location in the blood vessel network of a patient, comprising:
   a. a flexible microcatheter, including:
      i. a proximal double lumen portion;
      ii. a distal single lumen portion, holding said medical device in a contracted state;
   b. first wire, extending into a first lumen of said proximal double lumen portion and being attached to said medical device at a first attachment point, such that said first wire can push and pull said first attachment point and a second wire extending into a second lumen of said proximal double lumen portion and being attached to said medical device at a second attachment point, spaced apart from said first attachment point, such that said second wire can push and pull said second attachment point, independent of said first wire; and
   c. a control unit, having a first wire control handle affixed to said first wire and a second wire control handle affixed to said second wire, each control handle being capable of pushing its affixed wire distally through said corresponding lumen or retracting its wire proximally through said corresponding lumen, and where said first and second wire control handles can be rotated together to any rotational position; and
   d. whereby said wires may be advanced in a distal manner to push said medical device out of said distal lumen and said medical device may then be manipulated by changing relative position of said control handles both in translation and rotation to manipulate and implant said medical device.

2. The assembly of claim 1, wherein said flexible microcatheter further includes a single lumen portion, proximal to said proximal double lumen portion.

3. The assembly of claim 1, wherein said medical device is an aneurysm closure device.

4. The assembly of claim 1, wherein said single lumen has a length of between 100 cm and 200 cm.

5. The assembly of claim 1, wherein said single lumen has a hydrophilic exterior surface.

6. The assembly of claim 1, wherein said lumen has an exterior diameter of between 1 mm and 2 mm.

7. The assembly of claim 1, wherein said first wire control handle and said second wire control handle are both greatly expanded in transverse dimension in comparison with said first wire and said second wire.

* * * * *

UNITED STATES PATENT AND TRADEMARK OFFICE
CERTIFICATE OF CORRECTION

PATENT NO. : 8,876,863 B2  
APPLICATION NO. : 14/013964  
DATED : November 4, 2014  
INVENTOR(S) : Joe Michael Eskridge It is certified that error appears in the above-identified patent and that said Letters Patent is hereby corrected as shown below:

In the Claims
In column 10, line 27 "claim 1" should read --claim 2--.

Signed and Sealed this
Twenty-second Day of March, 2016

Michelle K. Lee
*Director of the United States Patent and Trademark Office*